United States Patent
Lee et al.

(10) Patent No.: US 10,023,721 B2
(45) Date of Patent: Jul. 17, 2018

(54) DENTAL GLASS-IONOMER CEMENT COMPOSITION AND METHOD OF PREPARING THE SAME

(71) Applicant: SPIDENT CO., LTD., Incheon (KR)

(72) Inventors: Na Ri Lee, Incheon (KR); Ki Hoon Kim, Incheon (KR); Jae Hwan Kim, Incheon (KR); Do Weon Lee, Incheon (KR); Min-Sung Kim, Incheon (KR)

(73) Assignee: SPIDENT CO., LTD., Incheon (KR)

( * ) Notice: Subject to any disclaimer, the term of this patent is extended or adjusted under 35 U.S.C. 154(b) by 0 days.

(21) Appl. No.: 14/941,606

(22) Filed: Nov. 15, 2015

(65) Prior Publication Data
US 2016/0152795 A1    Jun. 2, 2016

(30) Foreign Application Priority Data
Nov. 27, 2014    (KR) .................. 10-2014-0167565

(51) Int. Cl.
*C08K 3/40* (2006.01)
*C09D 135/00* (2006.01)
*A61K 6/00* (2006.01)
*A61K 6/083* (2006.01)

(52) U.S. Cl.
CPC .............. *C08K 3/40* (2013.01); *A61K 6/0091* (2013.01); *A61K 6/0835* (2013.01); *C09D 135/00* (2013.01)

(58) Field of Classification Search
None
See application file for complete search history.

(56) References Cited

U.S. PATENT DOCUMENTS

| | | | | |
|---|---|---|---|---|
| 3,028,247 A * | 4/1962 | Molnar | ................ | A61K 6/0023 106/35 |
| 4,089,830 A * | 5/1978 | Tezuka | ................. | A61K 6/0835 106/35 |
| 4,775,592 A * | 10/1988 | Akahane | .............. | A61K 6/0017 428/406 |
| 4,900,697 A * | 2/1990 | Akahane | .............. | A61K 6/0023 106/35 |
| 5,063,257 A * | 11/1991 | Akahane | .............. | A61K 6/0835 522/120 |

(Continued)

FOREIGN PATENT DOCUMENTS

| | | | | |
|---|---|---|---|---|
| EP | 0329268 A2 * | 8/1989 | ........... | A61K 6/0835 |
| EP | 0694298 B1 | 6/2010 | | |

(Continued)

OTHER PUBLICATIONS

MSDS Ketac-Molar, Nov. 3, 2014, 3M Company (Year: 2014).*
(Continued)

*Primary Examiner* — Peter A Salamon
(74) *Attorney, Agent, or Firm* — The PL Law Group, PLLC

(57) ABSTRACT

Disclosed is a dental glass-ionomer cement composition, which includes polycarboxylic acid, water, and a glass powder including a metal component that is able to form an ionic bond with a carboxyl group of polycarboxylic acid in the presence of water and having a polymer material that is applied on at least a portion of the surface of the glass powder. The dental glass-ionomer cement composition can guarantee sufficient working time and can exhibit increased initial strength.

14 Claims, 3 Drawing Sheets

(56) References Cited

U.S. PATENT DOCUMENTS

| | | | | |
|---|---|---|---|---|
| 5,296,026 | A * | 3/1994 | Monroe | A61C 8/0012 106/35 |
| 5,520,725 | A * | 5/1996 | Kato | A61K 6/0023 106/35 |
| 6,214,101 | B1 * | 4/2001 | Nakaseko | A61K 6/0017 106/35 |
| 6,264,472 | B1 * | 7/2001 | Okada | A61K 6/0017 433/228.1 |
| 6,719,834 | B1 * | 4/2004 | Braun | A61K 6/0835 106/35 |
| 6,756,421 | B1 * | 6/2004 | Todo | A61K 6/0023 523/115 |
| 2003/0136303 | A1 * | 7/2003 | Kobayashi | A61K 6/0835 106/35 |
| 2004/0067359 | A1 * | 4/2004 | Hirasawa | A61K 6/0276 428/391 |
| 2009/0012209 | A1 * | 1/2009 | Eckhardt | A61K 6/0017 523/116 |
| 2010/0036075 | A1 * | 2/2010 | Ishino | A61K 6/0023 526/320 |
| 2016/0152795 | A1 * | 6/2016 | Lee | A61K 6/0091 523/116 |

FOREIGN PATENT DOCUMENTS

| | | | | |
|---|---|---|---|---|
| EP | 2764859 A2 * | 8/2014 | | A61K 6/0835 |
| JP | H11-228327 A | 8/1999 | | |
| JP | 2002-541079 A | 12/2002 | | |
| JP | 2013-028568 A | 2/2013 | | |
| JP | 2014-152179 A | 8/2014 | | |
| KR | 10-0341142 A | 6/2002 | | |
| KR | 10-0341142 B1 | 6/2002 | | |
| KR | 10-2010-0138683 A | 12/2010 | | |
| KR | 10-2014-0042751 A | 4/2014 | | |
| WO | WO94/23687 A1 | 10/1994 | | |

OTHER PUBLICATIONS

Ketac Molar Easymix,3M ESPE, 2004 (Year: 2004).*
Office action dated Jan. 4, 2016 from Korean Intellectual Property Office in a counterpart Korean Patent Application No. 10-2014-0167565 (all the cited references are listed in this IDS).
Office action dated May 30, 2017 from Japan Intellectual Property Office in a counterpart Japanese Patent Application No. 2016-554579 (all the cited references are listed in this IDS.).

* cited by examiner

DENTAL GLASS-IONOMER CEMENT COMPOSITION AND METHOD OF PREPARING THE SAME

CROSS-REFERENCE TO RELATED APPLICATION

This application claims priority to and the benefit of Korean Patent Application No. 10-2014-0167565, filed on Nov. 27, 2014, the disclosure of which is incorporated herein by reference in its entirety.

BACKGROUND

1. Field of the Invention

The present invention relates to a dental glass-ionomer cement composition and a method of preparing the same and, more particularly, to a dental glass-ionomer cement composition and a method of preparing the same, in which the dental glass-ionomer cement composition may exhibit increased initial strength while ensuring sufficient working time by a user.

2. Description of the Related Art

Dental glass-ionomer cement is characterized by high biocompatibility, strong adhesion to teeth, and a good esthetic appearance. Also, dental glass-ionomer cement is responsible for gradually releasing fluorine to thus strengthen the tooth structure, and is thus widely utilized in various dental fields. Dental glass-ionomer cement is composed mainly of a fluoroaluminosilicate glass powder and a polycarboxylic acid aqueous solution. More specifically, the polycarboxylic acid aqueous solution may dissolve the surface of a glass powder such as fluoroaluminosilicate, so that the metal in the glass, such as alkali metal, alkaline earth metal, or aluminum, is isolated as ions, and these ions are used to form an ionic bond with the carboxyl group of polycarboxylic acid to thus yield a cross-linked structure.

Typically, a glass ionomer includes an aqueous solution of a polyacrylic acid derivative as polycarboxylic acid and an inorganic filler comprising a fluoroaluminosilicate powder, and the above two materials are mixed immediately before use. Upon mixing, the protons in the aqueous solution infiltrate the inorganic powder, whereby the cations of the inorganic powder are substituted and released. The cations and the carboxylate anions of the polyacrylic acid derivative are subjected to an acid-base reaction to form a chelate, and thus setting occurs for a few minutes after mixing. Furthermore, fluorine, contained in a small amount in the inorganic powder, is gradually released over a long period of time, thus exhibiting cavity preventive effects.

Despite the above advantages, however, the glass ionomer has low initial strength, and the setting thereof wholly depends on the formation of the chelate, undesirably resulting in poor mechanical properties, and moreover, the setting reaction begins at the time of mixing, undesirably resulting in a working time as short as a few minutes.

With regard to the glass-ionomer cement composition, Korean Patent No. 10-0341142 (Jun. 20, 2002) discloses a novel polymerizable carboxylic acid (meth)acrylate monomer for dental restorative materials exhibiting improved mechanical properties and ease of use, a method of preparing the same, and a dental restorative composition including the same, and also, Korean Patent Application Publication No. 10-2014-0042751 (Apr. 7, 2014) discloses a fluoroaluminosilicate glass powder for increasing acid resistance of a dental glass-ionomer cement and a method of preparing the same.

Meanwhile, with the goal of solving the defects of the conventional glass ionomer, including low initial strength and poor mechanical properties, by using photopolymerization and acid-base reaction together upon setting, a resin-reinforced glass ionomer has been developed. Furthermore, a photocurable resin-reinforced glass ionomer has been developed, in which a mixture of an aqueous solution and inorganic powder is loaded in a tooth portion to be treated and is then irradiated with light to thus be cured.

However, the conventional techniques are problematic because the working time is still short, and many attempts are being continuously made to increase the initial compressive strength.

SUMMARY

Accordingly, the present invention has been made keeping in mind the above problems encountered in the related art, and an object of the present invention is to provide a dental glass-ionomer cement composition and a method of preparing the same, in which sufficient working time of the glass ionomer may be ensured and the initial strength thereof may be increased.

The present invention provides a dental glass-ionomer cement composition, comprising: polycarboxylic acid; water; and a glass powder comprising a metal component that is able to form an ionic bond with a carboxyl group of the polycarboxylic acid in the presence of water, and including a polymer material that is applied on at least a portion of a surface of the glass powder.

In an embodiment, the polycarboxylic acid may have at least one of repeating units represented by Chemical Formulas 1 to 3 below:

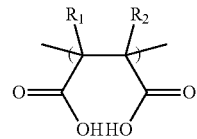

[Chemical Formula 1]

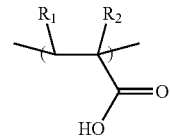

[Chemical Formula 2]

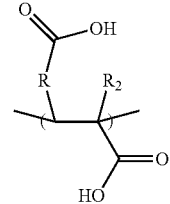

[Chemical Formula 3]

wherein $R_1$ and $R_2$ are identical to or different from each other, and are each independently any one selected from among hydrogen, a substituted or unsubstituted C1-C20 alkyl group, a substituted or unsubstituted C6-C18 aryl group, a substituted or unsubstituted C7-C30 aralkyl group, and a silyl group having substituted or unsubstituted C1-C30 alkyl or C6-C24 aryl, and R is any one selected from among a substituted or unsubstituted C1-C20 alkylene group, a substituted or unsubstituted C6-C18 arylene group, and a substituted or unsubstituted C7-C30 aralkylene group.

In an embodiment, the polycarboxylic acid may be obtained by polymerizing or copolymerizing any one or a mixture of two or more selected from among acrylic acid, methacrylic acid, maleic acid, maleic anhydride, fumaric acid, and itaconic acid.

In an embodiment, the metal component of the glass powder, which is able to form an ionic bond with the carboxyl group of the polycarboxylic acid, may comprise any one or more selected from among an alkali metal, an alkaline earth metal, a transition metal, and aluminum.

In an embodiment, the polymer material, which is applied on the glass powder, may be obtained by polymerizing a monomer having a carboxyl group, and may be applied in an amount of 0.2 to 30 parts by weight based on 100 parts by weight of the glass powder.

In an embodiment, the polymer material, which is applied on the glass powder, may have a larger number average molecular weight than a number average molecular weight of the polycarboxylic acid.

In an embodiment, the dental glass-ionomer cement composition may further comprise a fluorine component.

In an embodiment, the dental glass-ionomer cement composition may comprise, based on 100 parts by weight of the polycarboxylic acid, 20 to 500 parts by weight of water and 25 to 1000 parts by weight of the glass powder.

In an embodiment, the dental glass-ionomer cement composition may further comprise: a polymerizable monomer; and a chemical polymerization catalyst or photopolymerization catalyst, wherein the polymerizable monomer is polymerized using the catalyst.

In addition, the present invention provides a method of preparing a dental glass-ionomer cement composition, comprising: applying a polymer material on a surface of a glass powder curable in the presence of polycarboxylic acid and water; and mixing a composition A, comprising the glass powder including the polymer material applied on the surface thereof, with a composition B, comprising polycarboxylic acid, in the presence of water.

According to the present invention, a dental glass-ionomer cement composition can be provided, which exhibits increased initial strength and enables sufficient working time to be ensured when a user works or provides treatment.

Also, according to the present invention, a method of economically preparing the dental glass-ionomer cement composition can be provided.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
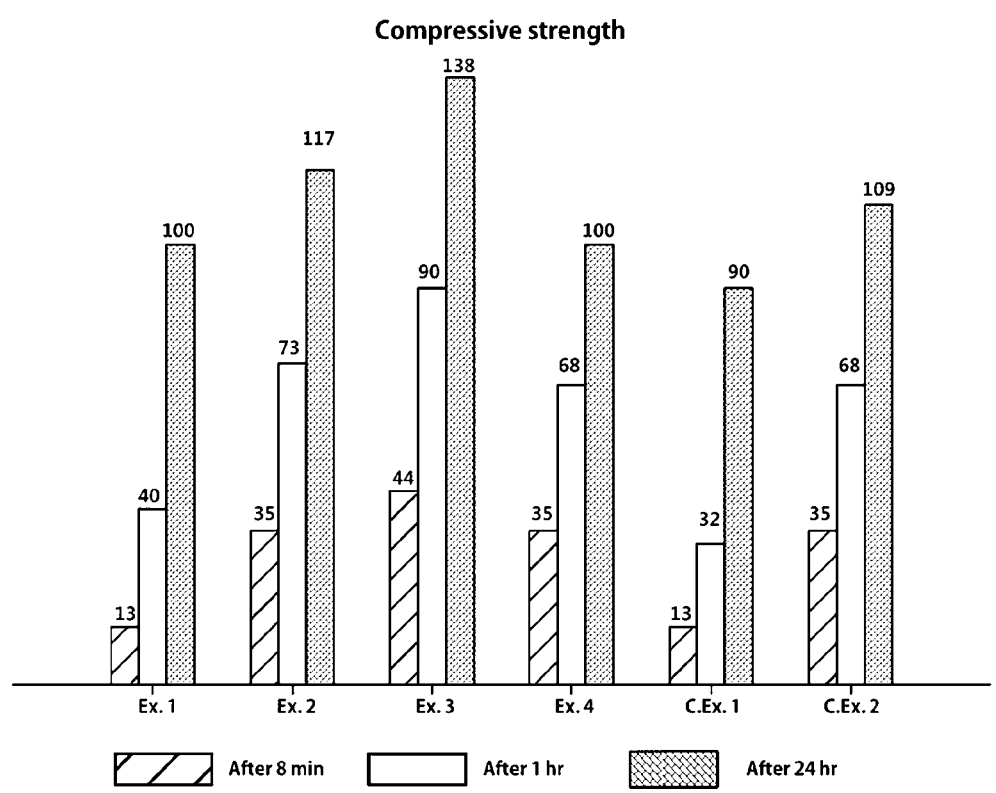
FIG. 1 illustrates the results of evaluating the compressive strength of glass ionomers according to the present invention and conventional glass ionomers.

Hereinafter, a detailed description will be given of embodiments of the present invention with reference to the appended drawings so that the present invention may be easily carried out by those skilled in the art to which the present invention belongs. In the following description of the present invention, detailed descriptions of known constructions and functions incorporated herein will be omitted when it may make the gist of the present invention unclear.

The present invention addresses a dental glass-ionomer cement composition, which may exhibit increased initial strength and ensure sufficient working time when a user works or provides treatment. More particularly, the glass-ionomer cement composition according to the present invention comprises polycarboxylic acid, water, and a glass powder comprising a metal component that is able to form an ionic bond with a carboxyl group of polycarboxylic acid in the presence of water and including a polymer material that is applied on at least a portion of the surface of the glass powder.

In the glass-ionomer cement composition, polycarboxylic acid functions as an acid in the presence of water, and the glass powder behaves as a base, and water plays a role in transporting ions that essentially exist in the ionic reaction.

Thus, the glass-ionomer cement composition according to the present invention is obtained by mixing a composition A, comprising the glass powder, with a composition B, comprising polycarboxylic acid, and the acid-base reaction spontaneously occurs throughout the mixing process, so that the mixture is solidified, thus sufficiently completing a setting reaction within a period of about a day.

In this regard, literature [Prosser et al., J. Chem. Tech. Biotechnol., 29, 69-87(1979)] is referenced. A chelating agent such as tartaric acid is known to adjust the solidification rate, and a dry atmosphere has to be maintained during the solidification time.

Useful in the present invention, polycarboxylic acid may be obtained by polymerizing a monomer having a carboxyl group.

More specifically, the monomer having a carboxyl group may be a monomer having a polymerizable ethylenically unsaturated group or a polymerizable epoxy group, but the present invention is not limited thereto. Preferably useful is an ethylenically unsaturated group. In particular, an ethylenically unsaturated group, which may be polymerized by a free radical mechanism, is utilized.

Examples of the unsaturated group may include a substituted or unsubstituted acrylate, a substituted or unsubstituted methacrylate, a substituted or unsubstituted alkene, and a substituted or unsubstituted acrylamide.

More specifically, the polycarboxylic acid may include a homopolymer or copolymer of unsaturated mono-, di-, or tri-carboxylic acid.

In the present invention, the polycarboxylic acid may have at least one of the repeating units represented by Chemical Formulas 1 to 3 below, and may be obtained by polymerizing or copolymerizing a monomer having an ethylenically unsaturated group that is able to form a saturated bond of a main chain in the repeating unit.

[Chemical Formula 1]

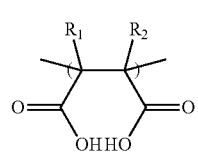

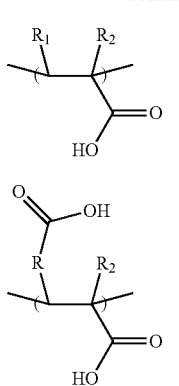

[Chemical Formula 2]

[Chemical Formula 3]

In Chemical Formulas 1 to 3, $R_1$ and $R_2$ are identical to or different from each other, and may be each independently any one selected from among hydrogen, a substituted or unsubstituted C1-C20 alkyl group, a substituted or unsubstituted C6-C18 aryl group, a substituted or unsubstituted C7-C30 aralkyl group, and a silyl group having substituted or unsubstituted C1-C30 alkyl or C6-C24 aryl, and R may be any one selected from among a substituted or unsubstituted C1-C20 alkylene group, a substituted or unsubstituted C6-C18 arylene group, and a substituted or unsubstituted C7-C30 aralkylene group.

As used herein, the term 'substituted' of 'substituted or unsubstituted' means that hydrogen of the aryl group or alkyl group is substituted with at least one substituent selected from among a C1-C20 alkyl group, a C6-C18 aryl group, a C1-C20 alkoxy group, a C7-C18 aralkyl group, a silyl group having C1-C10 alkyl or C6-C12 aryl, halogen, and a carboxyl group.

In the present invention, taking into consideration the range of the alkyl group or the aryl group in the 'substituted or unsubstituted C1-C20 alkyl group' or 'substituted or unsubstituted C6-C12 aryl group', the number of carbons in each of the C1-C20 alkyl group and the C6-C12 aryl group indicates the total number of carbons in the alkyl or aryl moiety in an unsubstituted condition, without considering the portion substituted with a substituent. For example, a phenyl group, the para position of which is substituted with a butyl group, corresponds to a C6 aryl group substituted with a C4 butyl group.

Used in the compound of the present invention, an aryl group is an organic radical derived from an aromatic hydrocarbon by the removal of one hydrogen atom, and includes a 5- or 6-membered single or fused ring system. When a substituent is provided in the aryl group, it may be fused with an adjacent substituent, thus additionally forming a ring.

Specific examples of the aryl may include, but are not limited to, phenyl, naphthyl, biphenyl, terphenyl, anthryl, indenyl, fluorenyl, and phenanthryl.

At least one hydrogen atom of the aryl group may be substituted with at least one substituent selected from among a C1-C20 alkyl group, a C6-C18 aryl group, a C1-C20 alkoxy group, a C7-C18 aralkyl group, a silyl group having C1-C10 alkyl or C6-C12 aryl, halogen, and a carboxyl group.

As the substituent used in the present invention, an alkyl group refers to a radical in which a hydrogen atom is removed from alkane, and specific examples thereof may include methyl, ethyl, propyl, iso-butyl, sec-butyl, tert-butyl, pentyl, iso-amyl, hexyl, etc., and at least one hydrogen atom of the alkyl group may be substituted with the substituent as exemplified in the above aryl group.

Specific examples of the silyl group, which is the substituent used in the compound of the present invention, may include trimethylsilyl, triethylsilyl, triphenylsilyl, trimethoxysilyl, dimethoxyphenylsilyl, diphenylmethylsilyl, diphenylvinylsilyl, and methylcyclobutylsilyl, and at least one hydrogen atom of the silyl group may be substituted with the substituent as exemplified in the above aryl group.

The repeating unit represented by Chemical Formula 1 or 2 corresponds to the main component of polycarboxylic acid in the present invention, and may be used alone. For copolymerization, an additional repeating unit may be used.

In the present invention, polycarboxylic acid has a number average molecular weight ranging from 1,000 to 1,000,000, and preferably 5,000 to 150,000.

More specifically, the polycarboxylic acid may be obtained by polymerizing or copolymerizing any one or a mixture of two or more selected from among acrylic acid, methacrylic acid, maleic acid, maleic anhydride, fumaric acid, itaconic acid, 2-chloroacrylic acid, 3-chloroacrylic acid, 2-bromoacrylic acid, 3-bromoacrylic acid, glutaconic acid, aconitic acid, citraconic acid, mesaconic acid, and tiglic acid.

Here, the unsaturated monomer for copolymerization may include an unsaturated aliphatic compound, such as acrylamide, acrylonitrile, vinyl chloride, aryl chloride, vinyl acetate, and 2-hydroxyethyl methacrylate.

Preferred examples of polycarboxylic acid include a homopolymer of acrylic acid or methacrylic acid, and copolymers of acrylic acid and itaconic acid, methacrylic acid and itaconic acid, acrylic acid and maleic acid, and fumaric acid, acrylic acid and maleic anhydride or maleic acid.

As the glass powder used in the present invention, any type of glass powder may be used without limitation so long as it includes a metal component able to form an ionic bond with a carboxyl group of polycarboxylic acid in the presence of water.

The metal component of the glass powder corresponds to a cation able to react with a carboxyl group, and may include any one or more selected from among alkali metal, alkaline earth metal, transition metal, and aluminum.

Examples of the alkali metal may include Li, Na, K, Rb, and Cs, and examples of the alkaline earth metal may include Mg, Ca, Sr, and Ba. The transition metal is exemplified by a transition metal from Groups 3 (3B) to 12 (2B).

The glass powder may contain a fluorine component for exhibiting fluoride release effects.

A preferable example of the glass powder includes a fluoroaluminosilicate glass powder, which is composed specifically of, based on the total weight of the glass, 10 to 25 wt % of $Al^{3+}$, 5 to 30 wt % of $Si^{4+}$, 1 to 30 wt % of $F^-$, 0 to 20 wt % of $Sr^{2+}$, 0 to 20 wt % of $Ca^{2+}$, and 0 to 10 wt % of alkaline earth metal ($Na^+$, $K^+$). In order to incorporate these ingredients in the glass powder, materials containing the above ingredients are mixed, melted, cooled, and pulverized, thus obtaining the glass powder.

By virtue of the pulverization process, the average particle size of the powder may be adjusted to about 0.02 to 100 μm.

The powder of the glass ionomer is dissolved in an acid. For example, calcium fluoroaluminosilicate glass may comprise 30 to 40% of $SiO_2$, 20 to 30% of $Al_2O_3$, 0 to 3% of $AlF_3$, 10 to 20% of $CaF_2$, 0 to 10% of NaF, 0 to 12% of $AlPO_4$, 0 to 15% of $SrCO_3$, and 0 to 10% of $Ca_3(PO_4)_2$.

Also, the glass powder according to the present invention may include a typically useful pigment in an appropriate amount, as necessary.

In the present invention, an inorganic filler powder having a particle size of 0.02 to 100 μm may be added to enhance mechanical properties. Examples of the inorganic filler powder may include quartz, silica, alumina, hydroxyapatite, and titanium dioxide.

The composition according to the present invention may additionally include a polymerization inhibitor, a colorant, etc., as needed. Furthermore, an organic solvent such as acetone, ethanol, etc. may be added.

For the glass-ionomer cement composition according to the present invention, when the mixture of powder and liquid is polymerized, a polymerizable monomer for photopolymerization or chemical polymerization and a chemical polymerization catalyst or a photopolymerization catalyst may be mixed. Specifically, the glass-ionomer cement composition may further include a polymerizable monomer and a chemical polymerization catalyst or a photopolymerization catalyst. As the polymerizable monomer is polymerized by the catalyst, the glass-ionomer cement composition may be utilized as a resin-reinforced glass-ionomer cement composition, thus exhibiting improved properties.

The glass-ionomer cement composition according to the present invention comprises, based on 100 parts by weight of polycarboxylic acid, 20 to 500 parts by weight of water and 25 to 1,000 parts by weight of glass powder, preferably 50 to 200 parts by weight of water and 100 to 500 parts by weight of glass powder, and more preferably 80 to 100 parts by weight of water and 100 to 300 parts by weight of glass powder.

Meanwhile, the polymer material, which is applied on at least a portion of the surface of the glass powder in the present invention, may include a polymer material obtained by polymerizing a monomer having a carboxyl group.

Examples thereof may include, but are not limited to, polymers of one or more monomers selected from among acrylic acid, methacrylic acid, maleic acid, maleic anhydride, fumaric acid, itaconic acid, 2-chloroacrylic acid, 3-chloroacrylic acid, 2-bromoacrylic acid, and 3-bromoacrylic acid.

The polymer material may be used in an amount of 0.2 to 30 parts by weight, and preferably 0.5 to 15 parts by weight, based on 100 parts by weight of the glass powder.

The polymer material, which is applied on the glass powder, is responsible for delaying the reaction time between polycarboxylic acid and glass powder and is thus considered to affect the working time and the setting time. Also, this material has an influence on compressive strength and facilitates the mixing process.

The polymer material, which is applied on the glass powder, has a number average molecular weight of 1,000 to 1,000,000, and preferably has a number average molecular weight of 5,000 to 150,000 corresponding to the number average molecular weight of polycarboxylic acid.

As the number average molecular weight of polycarboxylic acid increases, high compressive strength (after 24 hr) may be manifested.

In addition, the present invention addresses a method of preparing the dental glass-ionomer cement composition.

The method includes applying a polymer material on the surface of a glass powder curable in the presence of polycarboxylic acid and water, and mixing a composition A, comprising the glass powder including the polymer material applied on the surface thereof, with a composition B comprising polycarboxylic acid, in the presence of water.

Specifically, the polymer material may be applied on the surface of the glass powder in such a manner that a typical glass powder is mixed with a polymer material solution and then the solvent is removed therefrom, a typical glass powder is immersed in a polymer material solution and then taken out of the polymer material solution, or a polymer material solution is sprayed onto a glass powder, but the present invention is not limited thereto.

For example, when the glass powder is mixed with the polymer material solution, water or an organic solvent may be used. Such an organic solvent may be exemplified by an alcohol such as methanol, ethanol, isopropanol or butanol, a ketone such as acetone or methylethylketone, or an ether such as tetrahydrofuran.

Also, the mixing of the composition A, including the glass powder, with the composition B, including polycarboxylic acid, in the presence of water is a reaction for preparing a glass ionomer, and water is essentially required for the reaction. As such, water may be contained in either the composition A or the composition B. Alternatively, the glass powder and the polycarboxylic acid may be mixed under anhydrous conditions and then added with water, thereby obtaining a glass ionomer.

Preferably, the glass powder and the polycarboxylic acid aqueous solution are mixed and reacted.

A better understanding of the present invention may be obtained through the following examples, which are set forth to illustrate, but are not to be construed to limit the present invention, as is apparent to those skilled in the art.

EXAMPLE 1

1.1 Preparation of Polycarboxylic Acid Aqueous Solution
100 mmol itaconic acid was placed in a 500 mL three-neck flask, added with an initiator potassium persulfate (10 wt %) and distilled water (30 wt %), and then stirred.

The reaction temperature was adjusted to 85° C., after which a mixture of 100 mmol acrylic acid and distilled water (35 wt %) was placed in a vial, stirred, and then added dropwise into the 500 mL three-neck flask.

After 3 hr, the extent of reaction was checked by GPC. After completion of the reaction, the temperature was gradually decreased. The reaction mixture was lyophilized to remove the solvent (distilled water), and the lyophilized reaction mixture was made into a 50% aqueous solution suitable for use in a glass-ionomer composition, yielding a polycarboxylic acid aqueous solution having a number average molecular weight of 8,000.

1.2 Coating of Glass Powder
6 g of polyacrylic acid (Sigma-Aldrich) having a number average molecular weight of 8,000, as a coating material, was placed in a 500 mL beaker, added with 100 mL of ethanol, and stirred, so that the polymer was completely dissolved.

100 g of calcium fluoroaluminosilicate glass was added to the ethanol solution and stirred for 1 hr. After completion of the reaction, the reaction mixture was quickly stirred at 150 rpm until the ethanol was evaporated. Then, the reaction product was pulverized using a mortar and a pestle.

1.3 Setting of Dental Glass-Ionomer Cement
2.7 g of the glass powder obtained in Section 1.2 and 1 g of the polycarboxylic acid aqueous solution obtained in Section 1.1 were mixed, thus obtaining a glass-ionomer cement composition.

EXAMPLE 2

This example was performed in the same manner as in Example 1, with the exception that polycarboxylic acid resulting from polymerizing acrylic acid and itaconic acid at a ratio of 2:1 was used.

EXAMPLE 3

This example was performed in the same manner as in Example 2, with the exception that polyacrylic acid having a number average molecular weight of 100,000 was used as the polymer material applied on the glass powder.

EXAMPLE 4

This example was performed in the same manner as in Example 2, with the exception that polyacrylic acid having a number average molecular weight of 2,000 was used as the polymer material applied on the glass powder.

COMPARATIVE EXAMPLE 1

This example was performed in the same manner as in Example 1, with the exception that the glass ionomer was prepared without coating the glass powder as in Section 1.2.

COMPARATIVE EXAMPLE 2

This example was performed in the same manner as in Example 2, with the exception that the glass ionomer was prepared without coating the glass powder as in Section 1.2.

Evaluation of Performance

1) Compressive Strength

The compressive strength of the obtained glass ionomer products was measured in accordance with medical device standards (ISO 9917). Specifically, a mold having a height of 6.0±0.1 mm and a diameter of 4.0±0.1 mm was used, and five samples were prepared. The samples were immersed in 3-grade water at 37±1° C. for 23±0.5 hr based on ISO 3696. After 24 hr, the flat portion of each sample was placed between the compression plates of a tester (D.1.5), a compressive load was applied along the long axis of the sample, the maximum load that was applied when the sample broke was recorded, and the compressive strength C was calculated in units of megapascals (MPa).

2) Setting Time

The setting time of the obtained glass ionomer products was measured in accordance with medical device standards (ISO 9917). 90 seconds after the completion of the mixing of the glass ionomer, an indentation machine was carefully placed on the surface of the cement, perpendicular thereto, and then allowed to remain there for 5 sec, after which the time that elapsed from the time point at which mixing was completed to the time point at which a completely circular indentation could not be formed on the cement using a needle was recorded as the setting time.

3) Working Time

The working time of the obtained glass ionomer products was measured in accordance with medical device standards (ISO 9917). 40 seconds after the completion of the mixing of the glass ionomer, an indentation machine was carefully placed on the surface of the cement, perpendicular thereto, and then allowed to remain there for 5 sec, after which the time that elapsed from the time point at which mixing was completed to the time point at which the cement could not be completely perforated by a needle was recorded as the working time.

The test results of Examples 1 to 4 and Comparative Examples 1 and 2 are given in Table 1 below.

TABLE 1

| No. | Monomers for polycarboxylic acid | M.W. of material applied on glass powder | Working time (min) | Setting time (min) | Compressive strength (after 8 min) | Compressive strength (after 1 hr) | Compressive strength (after 24 hr) |
| --- | --- | --- | --- | --- | --- | --- | --- |
| Ex. 1 | Acrylic acid + Itaconic acid at 1:1 | 8,000 | 2.3 | 5.2 | 13 | 40 | 100 |
| Ex. 2 | Acrylic acid + Itaconic acid at 2:1 | 8,000 | 2.3 | 5.2 | 35 | 73 | 117 |
| Ex. 3 | Acrylic acid + Itaconic acid at 2:1 | 100,000 | 2.5 | 5.5 | 44 | 90 | 138 |
| Ex. 4 | Acrylic acid + Itaconic acid at 2:1 | 2,000 | 1.5 | 3.5 | 35 | 68 | 100 |
| C. Ex. 1 | Acrylic acid + Itaconic acid at 1:1 | — | 1.0 | 2.0 | 13 | 32 | 90 |
| C. Ex. 2 | Acrylic acid + Itaconic acid at 2:1 | — | 1.0 | 2.5 | 35 | 68 | 109 |

Figure 2:
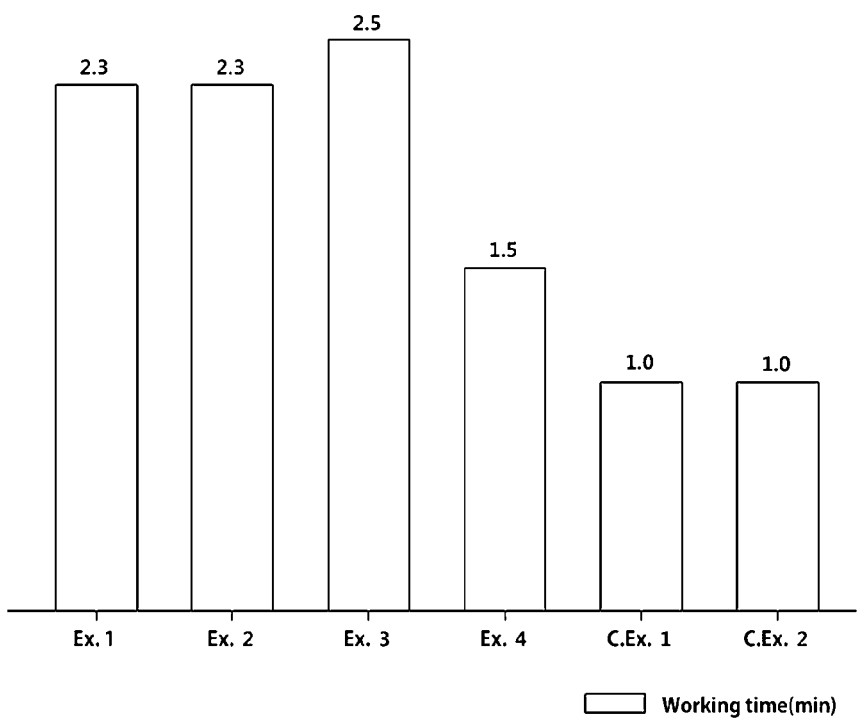
FIG. 2 illustrates the results of evaluating the working time of glass ionomers according to the present invention and conventional glass ionomers.
Figure 3:
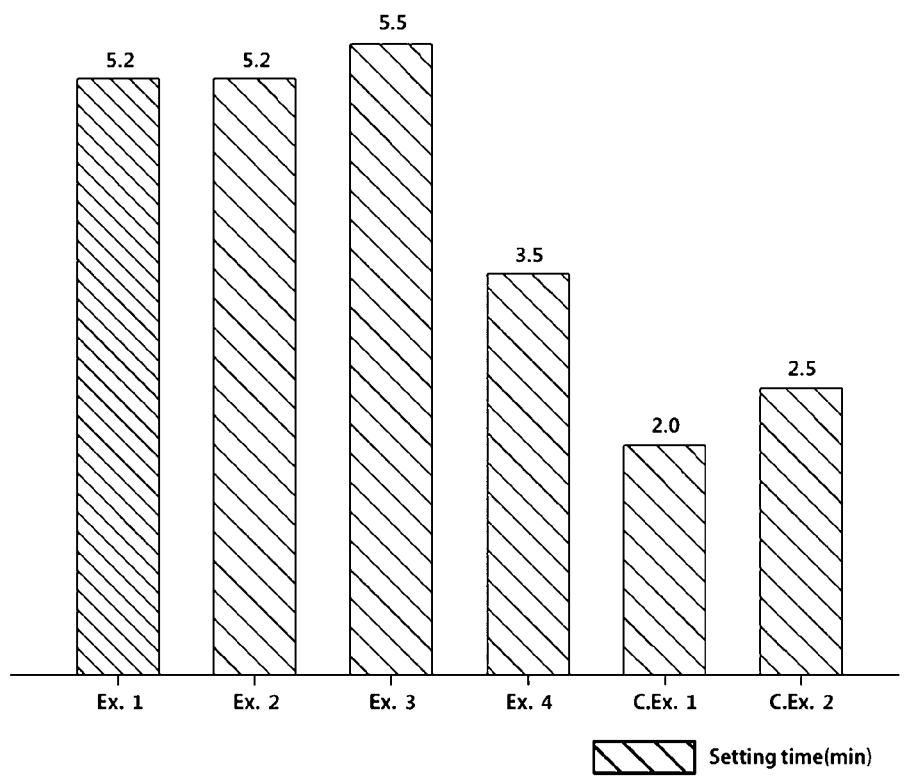
FIG. 3 illustrates the results of evaluating the setting time of glass ionomers according to the present invention and conventional glass ionomers.

The compressive strength results of Table 1 are shown in FIG. 1, the working time results of Table 1 are shown in FIG. 2, and the setting time results of Table 1 are shown in FIG. 3.

As is apparent from Table 1 and FIGS. 1 to 3, the glass ionomer according to the present invention was superior in initial compressive strength and compressive strength after one day, compared to the glass ionomer of Comparative Example 2. Furthermore, desired working time for use by a worker can be ensured.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A dental glass-ionomer cement composition, comprising:
polycarboxylic acid;
water; and
a glass powder comprising a metal component that is able to form an ionic bond with a carboxyl group of the polycarboxylic acid in presence of water, wherein at least a portion of a surface of the glass powder have been coated with a polymer, wherein the polymer is obtained by polymerizing a monomer having a carboxylic acid group, and the polymer is included in an amount of 6 parts by weight based on 100 parts by weight of the glass powder.

2. The dental glass-ionomer cement composition of claim 1, wherein the polycarboxylic acid has at least one of repeating units represented by Chemical Formulas 1 to 3 below:

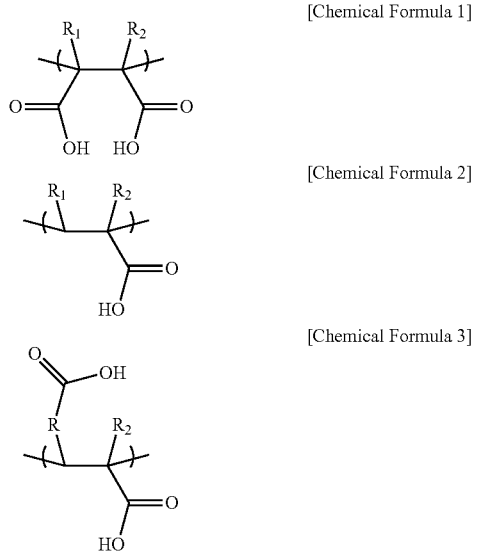

[Chemical Formula 1]

[Chemical Formula 2]

[Chemical Formula 3]

wherein $R_1$ and $R_2$ are identical to or different from each other, and are each independently any one selected from among hydrogen, a substituted or unsubstituted C1-C20 alkyl group, a substituted or unsubstituted C6-C18 aryl group, a substituted or unsubstituted C7-C30 aralkyl group, and a silyl group having substituted or unsubstituted C1-C30 alkyl or C6-C24 aryl; and
R is any one selected from among a substituted or unsubstituted C1-C20 alkylene group, a substituted or unsubstituted C6-C18 arylene group, and a substituted or unsubstituted C7-C30 aralkylene group.

3. The dental glass-ionomer cement composition of claim 1, wherein the polycarboxylic acid is obtained by polymerizing or copolymerizing any one or a mixture of two or more selected from among acrylic acid, methacrylic acid, maleic acid, maleic anhydride, fumaric acid, and itaconic acid.

4. The dental glass-ionomer cement composition of claim 1, wherein the metal component of the glass powder, which is able to form an ionic bond with the carboxyl group of the polycarboxylic acid, comprises any one or more selected from among an alkali metal, an alkaline earth metal, a transition metal, and aluminum.

5. The dental glass-ionomer cement composition of claim 1, wherein the polymer material, which is applied on the glass powder, has a larger number average molecular weight than a number average molecular weight of the polycarboxylic acid.

6. The dental glass-ionomer cement composition of claim 1, further comprising a fluorine component.

7. The dental glass-ionomer cement composition of claim 1, wherein the dental glass-ionomer cement composition comprises, based on 100 parts by weight of the polycarboxylic acid, 20 to 500 parts by weight of water and 25 to 1000 parts by weight of the glass powder.

8. The dental glass-ionomer cement composition of claim 1, further comprising:
a polymerizable monomer; and
a chemical polymerization catalyst or photopolymerization catalyst,
wherein the polymerizable monomer is polymerized using the catalyst.

9. The dental glass-ionomer cement composition of claim 1, wherein said at least the portion of the surface of the glass powder coated with the polymer material is produced by a process selected from the group consisting of mixing the glass powder with a solution of the polymer material and removing a solvent of the solution, immersing the glass powder in the solution of the polymer material and taking the glass powder out of the solution, and spraying the solution of the polymer material onto the glass powder.

10. The dental glass-ionomer cement composition of claim 1, wherein the polymer material is formed by polymerizing a monomer selected from the group consisting of acrylic acid, methacrylic acid, maleic acid, maleic anhydride, fumaric acid, itaconic acid, 2-chloroacrylic acid, 3-chloroacrylic acid, 2-bromoacrylic acid, and 3-bromoacrylic acid.

11. A dental glass-ionomer cement composition produced by a process comprising:
coating at least a portion of a surface of a glass powder with a polymer material; and
after the coating, mixing the glass powder coated with the polymer material with polycarboxylic acid in the presence of water,
wherein the polymer material is obtained by polymerizing a monomer having a carboxylic acid group, and the polymer material is included in an amount of 6 parts by weight based on 100 parts by weight of the glass powder.

12. The dental glass-ionomer cement composition of claim 11, wherein the process further comprises, after the coating, polymerizing a monomer by using a chemical polymerization catalyst or a photopolymerization catalyst.

13. The dental glass-ionomer cement composition of claim 11, wherein the coating comprises a process selected from the group consisting of (i) mixing the glass powder with a solution of the polymer material and removing a solvent of the solution, (ii) immersing the glass powder in the solution of the polymer material and taking the glass powder out of the solution, and (iii) spraying the solution of the polymer material onto the glass powder.

14. The dental glass-ionomer cement composition of claim 11, wherein the polymer material is formed by polymerizing a monomer selected from the group consisting of acrylic acid, methacrylic acid, maleic acid, maleic anhydride, fumaric acid, itaconic acid, 2-chloroacrylic acid, 3-chloroacrylic acid, 2-bromoacrylic acid, and 3-bromoacrylic acid.

* * * * *